United States Patent [19]

Kummer et al.

[11] 4,021,463

[45] May 3, 1977

[54] REGENERATION AND SEPARATION OF RHODIUM-CONTAINING OR IRIDIUM-CONTAINING CATALYSTS FROM DISTILLATION RESIDUES FOLLOWING HYDROFORMYLATION

[75] Inventors: Rudolf Kummer, Frankenthal; Kurt Schwirten, Ludwigshafen, both of Germany; Hans-Dieter Schindler, deceased, late of Frankenthal, Germany; by Maria Elisabeth Schindler; by Ute Lang, both of Neuried, Germany; by Rainer Schindler, heirs-at-law, Hechendorf, Germany

[73] Assignee: BASF Aktiengesellschaft, Ludwigshafen (Rhine), Germany

[22] Filed: Sept. 24, 1975

[21] Appl. No.: 616,448

[30] Foreign Application Priority Data

Oct. 9, 1974 Germany .......................... 2448005

[52] U.S. Cl. ........................... 260/429 R; 252/413; 260/604 HF
[51] Int. Cl.$^2$ ........................................ C07F 15/00
[58] Field of Search .............. 260/429 R, 606.5 P, 260/604 HF; 252/413

[56] References Cited

UNITED STATES PATENTS

| | | | |
|---|---|---|---|
| 3,515,757 | 6/1970 | Sibert | 260/429 R X |
| 3,547,964 | 12/1970 | Olivier | 260/429 R |
| 3,560,539 | 2/1971 | Booth | 260/429 R |
| 3,755,393 | 8/1973 | Kniese et al. | 260/429 R |

*Primary Examiner*—Helen M. S. Sneed
*Attorney, Agent, or Firm*—Johnston, Keil, Thompson & Shurtleff

[57] ABSTRACT

Regeneration and separation of catalysts $Me(CO)(PR_3)_2Hal$ (I) and $HMe(CO)(PR_3)_3$ (II), where Me is rhodium or iridium, Hal is halogen and R denotes the same or different hydrocarbon radicals, from distillation residues of hydroformylation mixtures by treating said residues with aqueous acids and peroxides, mixing the resulting Me salt solutions with water-soluble organic solvents and with a phosphine $PR_3$ and, in the case of the preparation of compound I, with a hydrohalic acid or an alkali metal halide, reacting the solutions at from 0° to 150° C and from 1 to 250 bars in case I with carbon monoxide or compounds eliminating carbon monoxide and in case II additionally with hydrogen, and separating the resulting compound I or II.

6 Claims, No Drawings

REGENERATION AND SEPARATION OF RHODIUM-CONTAINING OR IRIDIUM-CONTAINING CATALYSTS FROM DISTILLATION RESIDUES FOLLOWING HYDROFORMYLATION

The present invention relates to a novel process for regeneration and separation of rhodium-containing or iridium-containing catalysts from distillation residues such as are produced in the hydroformylation of olefins with carbon monoxide and hydrogen.

It is generally known to react olefins at elevated temperature and pressure with carbon monoxide and hydrogen in the presence of specific catalytically active metal carbonyl complexes to form aldehydes according to the following equation:

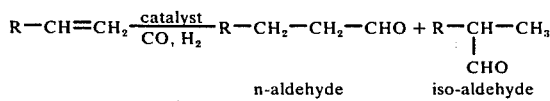
n-aldehyde     iso-aldehyde where R is an organic radical.

If, as commonly practised, cobalt-containing catalysts are used, the reaction temperatures required are relatively high, thus favoring the formation of the usually undesirable iso-aldehydes. Catalysts containing rhodium or iridium allow the use of much milder reaction conditions, thus giving the n-aldehydes in larger quantities (see "Catalyst Review", Vol. 6, 1972, page 68), but these catalysts have not yet been generally adopted in large-scale hydroformylations because the recovery and regeneration of the expensive noble metals presents considerable difficulties.

In both the batchwise and continuous processes the more volatile components of the reaction mixture, including the products of the process, are separated by distillation, whilst the catalyst accumulates in the higher-boiling distillation residue. Although this catalyst-containing residue may be recycled to the hydroformylation process, it is not possible to return the entire amount over a period of time, since the residue increases continuously and the activity of the catalyst diminishes in the course of time.

Thus considerable economic significance is attached to the recovery and regeneration of the expensive noble metal catalysts, but the prior art processes have not been very satisfactory. Both in the process disclosed by German published application No. 2,262,885 (disintegration of the catalysts with steam at elevated temperature) and the process described in German published application No. 1,954,815 (adsorption of rhodium on basic ion exchangers), the noble metal is produced in the elementary form, using which the production of the active complex is highly laborious.

According to the process described in U.S. Pat. No. 3,547,964, the catalyst-containing distillation residue is treated with aqueous acids and peroxides, and the aqueous phase containing noble metal salts is separated and the excess peroxide destroyed by heating, whereupon the aqueous solution is reacted with carbon monoxide in the presence of an inert water-immiscible solvent and a chelating agent such as triphenylphosphine, under pressure. There is obtained an organic solution of a noble metal carbonyl complex which may be returned to the hydroformylation. However, this method is also unsatisfactory, because regeneration of the catalyst takes place in a system of 2 liquid phases and therefore proceeds too slowly or at insufficient yield. Moreover, this known method merely permits the production of solutions in which the catalyst consists of the central noble metal atom and the nonvalent ligands CO and L, where L is for example a tertiary phosphine. However, it is frequently preferred to use the hydrides of these catalysts, or, for reasons of stability, to use complexes in which an L is replaced by halogen.

It is an object of the present invention to separate rhodium and iridium from the distillation residues occurring in hydroformylations and reconverting said metals quantitatively to an active form in a simple manner.

It is a further obejct of the invention to recover catalysts of the type $$Me(CO)(Pr_3)_2Hal \qquad \qquad I,$$

where Me is rhodium or iridium, Hal is halogen and R denotes the same or different hydrocarbon radicals, by regeneration of the distillation residues.

We have found that catalysts of the type I $$Me(CO)(PR_3)_2Hal \qquad \qquad I,$$

where Me is rhodium or iridium, Hal is halogen and R denotes the same or different hydrocarbon radicals, are obtained in a pure form by regenerating aqueous Me salt solutions such as are obtained by treating distillation residues of hydroformylation mixtures with acids and peroxides followed by destruction of the peroxides, provided that these aqueous solutions are reacted with carbon monoxide or compounds donating carbon monoxide in the presence of a water-soluble organic solvent containing hydrohalic acids or alkali metal halides and tertiary phosphines $PR_3$ at from 0° to 150° C and preferably from 50° to 100° C and at from 1 to 250 bars, followed by separation of the precipitated compounds I.

We have also found that the compounds of type II $$HMe(CO)(PR_3)_3 \qquad \qquad II$$

which are related to said catalysts I may be obtained by simultaneously subjecting the aqueous starting solutions to hydrogenating conditions and separating the compound II after precipitation or by subjecting solutions of compound I in water-soluble organic solvents together with additional phosphine $PR_3$ to hydrogenating conditions and precipitating the resulting compound II by the addition of water.

The distillation residues produced in hydroformylations using rhodium-containing or iridium-containing catalysts substantially consist of high-boiling aldehydes, alcohols, aldols and carboxylic acids and usually contain from 0.001 to 1% of noble metal.

One hundred parts by weight of such residue are reacted, advantageously with thorough mixing, with from 10 to 1000 parts by weight of a 1% to 20% aqueous mineral acid and from 10 to 100 parts by weight of a peroxide at from 20° to 120° C.

Suitable mineral acids are, in particular, nitric acid and also sulfuric acid or, when it is desired to produce the chlorine complex of formula I, preferably hydrochloric acid in admixture with nitric acid. Suitable peroxides are those which decompose on heating, i.e. in particular, hydrogen peroxide and also alkali metal peroxides or persulfates and persulfuric acids. Organic peroxides may be used, e.g. benzoyl peroxide.

Following the oxidation, in which rhodium and iridium pass into the aqueous phase virtually quantitatively in the form of their salts, the aqueous phase is separated and the excess peroxide is destroyed by boiling in the usual manner.

The aqueous noble metal salt solution may then be concentrated to a smaller volume if necessary, whereupon a water-soluble organic solvent and the phosphine $PR_3$ are added.

The amount of phosphine added is at least the stoichiometric amount according to formula I, based on rhodium or iridium, but it is advantageous to add the phosphine in a molar excess of up to 100 times.

The function of the water-soluble organic solvent is to keep the phosphine in solution in the aqueous organic phase. Thus the amount of solvent depends on the amount of aqueous starting solution, on the type of solvent used, on the amount and nature of the phosphine and, to a certain extent, on the amount and nature of the other components of the aqueous phase as determined by the pretreatment. This amount varies from case to case but may be readily determined by simple experiments on model solutions containing no noble metal. It is advantageous not to exceed the required minimum amount to a substantial degree, but observations to date indicate that the success of the process of the invention is not impaired even when the proportion of water in the total system is only 10% by weight.

Examples of suitable water-soluble organic solvents are acetone, tetrahydrofuran and dioxane and, in particular, alcohols of from 1 to 4 carbon atoms such as methanol, ethanol, propanol, isopropanol, n-butan-1-ol, n-butan-2-ol, iso-butan-1-ol and iso-butan-2-ol. It is recommended that the phosphine be dissolved in the solvent and then added, in this form, to the aqueous rhodium or iridium salt solution.

The choice of phosphine $PR_3$ depends on the nature of the hydroformylation reaction in which the rhodium or iridium catalyst is to be used. Preferably use is made of those catalysts of type I or II in which the organic radicals of phosphine are the same or different alkyl, aralkyl, aryl or alkylaryl radicals of from 1 to 12 carbon atoms, the total number of carbon atoms in the phosphine being from 12 to 36. All of these phosphines, of which the hydrocarbon radicals may bear halogen atoms as substituents if desired or may be interrupted by oxygen atoms, are suitable for the present catalyst-regenerating process because they have the important property of being adequately soluble in homogeneous aqueous organic media but of forming halogen or hydride complexes with rhodium or iridium and carbon monoxide which are very sparingly soluble in said media. In this respect the chemical nature of the phosphines is of secondary importance, and the instruction to use preferably trialkyl phosphines of from 12 to 24 carbon atoms or, in particular, triphenylphosphine thus merely serves to express the fact that these phosphines have been widely adopted, as rhodium or iridium ligands, in hydroformylation techniques.

If the phosphines are very sparingly soluble in the aqueous organic medium, it may be advantageous to use a dispersing agent. In this case there are obtained not homogeneous solutions but fine dispersions which, however, behave as solutions.

In order to form the halo complexes I it is necessary for halogen ions to be present in at least stoichiometric amount and preferably in an excess of up to 100 times molar. The halogen ions, particularly chloride, bromide and iodied, are preferably introduced in the form of the hydrohalic acids or alkali metal halides, this being done, in the case of bromide or iodide, advantageously after the peroxide has been destroyed.

It is also advantageous to heat the aqueous organic solution prior to carbonylation to give the phosphine an opportunity to become added to the noble metal.

Carbon monoxide is then passed into the aqueous organic solution containing the noble metal-phosphine comples, phosphine and the halogen ions at a temperature of from 0° to 120° C and at from 1 to 250 bars and preferably just below the boiling temperature of the solution and at atmospheric pressure. The complexes I are precipitated virtually quantitatively, possibly together with some of the excess phosphine.

If carbonylation is carried out under hydrogenating conditions, there is obtained the similarly insoluble hydrido complexes II. To this end, use is made either of reducing agents donating hydride ions, e.g. sodium borohydride, at from 0° to 100° C at atmospheric pressure, or hydrogen at from 0° to 150° C at from 1 to 300 bars.

The halo complexes I may, if desired, be subsequently converted to the hydrido complexes II by dissolving them in water-soluble organic solvents, effecting hydrogenation and precipitating the hydrido complexes by the addition of water.

The catalysts I or II recovered and regenerated by the process of the invention are returned to the hydroformylation process, e.g. by adding them to the circulation of the distillation residue.

Our process makes it possible to use economically rhodiumcatalyzed or iridium-catalyzed hydroformylations, which are of importance in the chemical industry. It may be readily introduced into large scale synthesis and is particularly valuable for permitting the recovery of the catalyst in the form of the particularly important halo and hydrido complexes I and II.

For example, the process may be applied to the synthesis of mainly n-aldehydes from mono-olefins, such as propionldehyde fom ethylene, n-butyraldehyde from propylene and n-nonanal from octene, and it may also be applied, in particular, to the bis-hydroformylation of conjugated unsaturated compounds having olefinic double bonds, such as butadiene, a reaction which has not been successful economically using the conventional cobalt catalysts.

EXAMPLE 1

100 g of a distillation residue from the bis-hydroformylation of butadiene, which essentially consisted of a mixture of acetals, aldehydes, triphenylphosphines and the oxide thereof, which mixture boils at above 130° C/5mm, and 63 mg of rhodium in the form of the complex $Rh(CO)L_2Br$ (L = triphenylphosphine) were diluted with 100 g of toluene and reacted, with stirring, for one hour with 200 g of 1N hydrochloride acid and 60 g of 30% hydrogen peroxide at room temperature, whereupon the excess peroxide was destroyed by boiling for a further hour.

After cooling, the aqueous phase, which contained 97% of the rhodium originally present, was mixed with 2.5 g of sodium bromide and, at 50° C, with a solution of 5 g of triphenylphosphine (= 30 moles/gram atoms of rhodium) and 220 ml of methanol.

The solution was then heated for one hour at 100° C and carbon monoxide was then passed therethrough at atmospheric pressure and at a temperature of 60° C. Over approx. 30 minutes the rhodium complex $Rh(CO)L_2Br$ precipitated in the form of yellow crystals. These were filtered off and returned to the hydroformylation loop.

In this manner, a total of 90% of the rhodium was recovered. 4% remained in the distillation residue and 6% in the aqueous organic phase. These residual amounts were passed to a collector, from which they were worked up in conventional manner to metallic rhodium.

EXAMPLE 2

Example 1 was repeated except that the aqueous phase produced during oxidation was concentrated to 50% of its original volume and 200 ml of isopropanol were used in place of the methanol, to give a total recovery of rhodium of 97.7%.

EXAMPLE 3

100 g of a distillation residue from the hydroformylation of propylene, which contained 46 mg of rhodium in the form of the complex $HRhCOL_3$ (L denotes triphenylphosphine) were diluted with 100 g of toluene and reacted for 12 hours at room temperature with 200 g of 1N hydrochloric acid, 5 g of sodium chloride and 30 g of 30% hydrogen peroxide.

The excess peroxide was destroyed by boiling the aqueous phase for 2 hours, during which process it was concentrated to 30% of its original volume, whereupon a solution of 5 g of triphenylphosphine (equivalent to 40 moles/gram atoms of rhodium) and 150 ml of isopropanol was added.

The resulting solution was heated to the boil for a further hour, whereupon carbon monoxide was bubbled through at 60° C. The solution was then concentrated to about 50 ml. The resulting yellow crystals of $Rh(CO)L_2Cl$ were separated, dried and heated together with 0.3 g of sodium borohydride and 2 g of triphenylphosphine in 50 ml of isopropanol. 100 ml of water were then added to the solution to cause the hydrido complex $HRh(CO)L_3$ to precipitate.

The yield of recovered rhodium was 98.7%. The residual 1.3% remained in the organic phases.

EXAMPLE 4

In a manner similar to that described in Example 3, 200 g of distillation residue were oxidized with nitric acid and hydrogen peroxide to give 100 ml of an aqueous solution containing 85 mg of rhodium.

This solution was shaken for 1 hour at 50° C in an autoclave with 300 ml of isopropanol, 10 g od triphenylphosphine (equivalent to 50 moles/gram atoms of rhodium) and 50 ml of an aqueous formaldehyde solution (carbon monoxide-donating agent) and was then subjected to a hydrogen pressure of 200 bars at 50° C for 10 hours.

There was obtained a clear solution from which the rhodium had precipitated in the form of the complex $HRh(CO)L_3$. The yield of recovered rhodium was 92.5%.

EXAMPLE 5

In the manner described in Example 4 but without separation of the organic phase following the oxidative treatment, 96% of the rhodium was recovered in the form of $HRh(CO)L_3$.

EXAMPLE 6

In the manner described in Example 3 but using 10 g of benzoyl peroxide in place of hydrogen peroxide, 81.3% of the rhodium was recovered.

EXAMPLE 7

100 g of a distillation residue from the hydoformylation of propylene to n-butyraldehyde using the iridium complex $ClIr(CO)L_2$ (L denotes triphenylphosphine) were treated in the manner described in Example 3. The yield of recovered iridium in the form of yellow $ClIr(CO)L_2$ was 79.5%.

EXAMPLE 8

100 g of a distillation residue from the hydroformylation of propylene to n-butyraldehyde using the rhodium complex $HRh(CO)L_3'$ (L' denotes tri-n-octylphosphine) were worked up as in Example 3 but using tri-n-octylphosphine as the ligand. The yield of recovered rhodium was 94.0%.

We claim:

1. A process for regeneration of catalysts of the formula $HMe(CO)(PR_3)_3$, wherein Me denotes rhodium or iridium and R denotes the same or different hydrocarbon radicals, which comprises treating a distillation residue of a rhodium-catalyzed or iridium-catalyzed hydroformylation process with an aqueous mineral acid and a peroxide at 20°–120° C to convert the iridium or rhodium into their respective water soluble salts which pass virtually quantitatively into the aqueous phase, separating said aqueous phase from the distillation residue, destroying the peroxide in said aqueous phase, reacting the iridium or rhodium salts in the separated aqueous phase at 0°–150° bars with carbon monoxide or a carbon monoxide donor, a hydrohalic acid or an alkali metal halide, and a tertiary phosphine $PR_3$ wherein R has the above meanings in the presence of a water-soluble organic solvent to form the catalyst $Me(CO)(PR_3)_2Hal$, in which Me and R have the above meanings and Hal denotes chlorine, bromine or iodine, which catalyst precipitates in the reaction mixture, and hydrogenating the reaction mixture or said catalyst $Me(CO)(PR_3)_2Hal$ produced therein to produce the catalyst $HMe(CO)(PR_3)_3$.

2. A process for regeneration of catalysts of the formula $Me(CO)(PR_3)_2Hal$ and separation thereof in pure form, wherein Me denotes rhodium or iridium, Hal denotes chlorine, bromine or iodine, and R denotes the same or different hydrocarbon radicals, which comprises treating a distillation residue of a rhodium-catalyzed or iridium-catalyzed hydroformylation process with an aqueous mineral acid and a peroxide at 20°–120° C to convert the iridium or rhodium into their respective water soluble salts which pass virtually quantitatively into the aqueous phase, separating said aqueous phase from the distillation residue, destroying the peroxide in said aqueous phase, reacting the iridium or rhodium salts in the separated aqueous phase at 0°–150° C and 1–250 bars with carbon monoxide or a carbon monoxide donor, a hydrohalic acid or an alkali metal halide, and a tertiary phosphine $PR_3$ wherein R has the above meanings in the pressure of a water-soluble organic solvent to form said catalyst Me(CO)(PR$_3$)$_2$Hal, which precipitates in the reaction mixture, and separating the precipitated catalyst.

3. A process as claimed in claim 2 wherein said aqueous mineral acid is aqueous nitric or sulfuric acid, or an aqueous nitric or sulfuric acid, or an aqueous mixture of nitric acid and hydrochloric acid.

4. A process as claimed in claim 3 wherein said peroxide is hydrogen peroxide, an alkali metal peroxide, an alkali metal persulfate, persulfuric acid or an organic peroxide.

5. A process as claimed in claim 2 wherein each R respectively is an alkyl, aralkyl, aryl or alkylaryl radical respectively having 1–12 carbon atoms.

6. A process as claimed in claim 2 wherein said water soluble organic solvent is acetone, tetrahydrofuran, dioxane, methanol, ethanol, propanol, isopropanol, n-butan-1-ol, n-butan-2-ol, iso-butan-1-ol or iso-butan-2-ol.

* * * * *

UNITED STATES PATENT AND TRADEMARK OFFICE
CERTIFICATE OF CORRECTION

PATENT NO. : 4,021,463
DATED : May 3, 1977
INVENTOR(S) : Kummer et al

It is certified that error appears in the above-identified patent and that said Letters Patent are hereby corrected as shown below:

Column 6, line 41, "0°-150° bars" should read --0-150°C and 1-250 bars--
Column 7, line 1, "pressure" should read --presence--

Signed and Sealed this

Eleventh Day of April 1978

[SEAL]

Attest:

RUTH C. MASON
Attesting Officer

LUTRELLE F. PARKER
Acting Commissioner of Patents and Trademarks